(12) United States Patent
Hart et al.

(10) Patent No.: US 8,017,145 B2
(45) Date of Patent: Sep. 13, 2011

(54) EXFOLIATING PERSONAL CARE WIPE ARTICLE CONTAINING AN ARRAY OF PROJECTIONS

(75) Inventors: Richard Steven Hart, Naugatuck, CT (US); Liam Anthony Murray, Monroe, CT (US); Ewa Urszula Padlo, Derby, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 2311 days.

(21) Appl. No.: 10/846,239

(22) Filed: May 14, 2004

(65) Prior Publication Data

US 2005/0136099 A1 Jun. 23, 2005

(51) Int. Cl.
*A61F 13/00* (2006.01)
*A61K 9/70* (2006.01)
*A61K 8/02* (2006.01)
*A01N 25/34* (2006.01)

(52) U.S. Cl. .......................... 424/443; 424/402; 424/401
(58) Field of Classification Search .................. 424/443, 424/402, 401
See application file for complete search history.

(56) References Cited

U.S. PATENT DOCUMENTS

| | | |
|---|---|---|
| 3,905,863 A | 9/1975 | Ayers |
| 3,918,449 A | 11/1975 | Pistor |
| 3,964,482 A | 6/1976 | Gerstel et al. |
| 4,082,878 A | 4/1978 | Boe et al. |
| 4,180,232 A | 12/1979 | Hardigg |
| 4,381,963 A | 5/1983 | Goldstein et al. |
| 4,585,991 A | 4/1986 | Reid et al. |
| 4,637,859 A | 1/1987 | Trokhan |
| 4,784,737 A | 11/1988 | Ray et al. |
| 4,837,049 A | 6/1989 | Byers et al. |
| 5,134,079 A | 7/1992 | Cusack et al. |
| 5,156,591 A | 10/1992 | Gross et al. |
| 5,158,073 A | 10/1992 | Bukowski |
| 5,162,043 A | 11/1992 | Lew et al. |
| 5,198,192 A | 3/1993 | Saito et al. |
| 5,215,088 A | 6/1993 | Normann et al. |
| 5,250,023 A | 10/1993 | Lee et al. |
| 5,250,067 A | 10/1993 | Gelfer et al. |
| 5,256,360 A | 10/1993 | Li |
| 5,279,544 A | 1/1994 | Gross et al. |
| 5,318,557 A | 6/1994 | Gross |
| 5,362,307 A | 11/1994 | Guy et al. |
| 5,383,512 A | 1/1995 | Javis |
| 5,498,235 A | 3/1996 | Flower |
| 5,512,219 A | 4/1996 | Rowland et al. |
| 5,527,288 A | 6/1996 | Gross et al. |
| 5,551,953 A | 9/1996 | Lattin et al. |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,676,850 A | 10/1997 | Reed et al. |
| 5,681,580 A | 10/1997 | Jang et al. |
| 5,704,520 A | 1/1998 | Gross |
| 5,711,761 A | 1/1998 | Untereker et al. |
| 5,720,961 A * | 2/1998 | Fowler et al. ................ 424/401 |
| 5,728,089 A | 3/1998 | Lal et al. |
| 5,730,714 A | 3/1998 | Guy et al. |
| 5,735,273 A | 4/1998 | Kurnik et al. |
| 5,771,890 A | 6/1998 | Tamada |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,848,985 A | 12/1998 | Muroki |
| 5,848,990 A | 12/1998 | Cirelli et al. |
| 5,848,991 A | 12/1998 | Gross et al. |
| 5,855,801 A | 1/1999 | Lin et al. |
| 5,879,326 A | 3/1999 | Godshall et al. |
| 5,899,785 A | 5/1999 | Groten et al. |
| 5,938,684 A | 8/1999 | Lynch et al. |
| 5,964,729 A | 10/1999 | Choi et al. |
| 5,970,583 A | 10/1999 | Groten et al. |
| 5,971,841 A | 10/1999 | Tintelnot |
| 6,023,629 A | 2/2000 | Tamada |
| 6,036,659 A | 3/2000 | Ray et al. |
| 6,038,465 A | 3/2000 | Melton, Jr. |
| 6,047,208 A | 4/2000 | Flower |
| 6,083,196 A | 7/2000 | Trautman et al. |
| 6,091,975 A | 7/2000 | Daddona et al. |
| 6,106,751 A | 8/2000 | Talbot et al. |
| 6,129,696 A | 10/2000 | Sibalis |
| 6,132,755 A | 10/2000 | Eicher et al. |
| 6,219,574 B1 | 4/2001 | Cormier et al. |
| 6,256,533 B1 | 7/2001 | Yuzhakov et al. |
| 6,294,182 B1 | 9/2001 | Znaiden et al. |
| 6,312,612 B1 | 11/2001 | Sherman et al. |
| 6,334,856 B1 | 1/2002 | Allen et al. |
| 6,361,784 B1 | 3/2002 | Brennan et al. |

(Continued)

FOREIGN PATENT DOCUMENTS

DE 2319591 11/1974

(Continued)

*Primary Examiner* — Isis Ghali

(74) *Attorney, Agent, or Firm* — Milton L. Honig

(57) ABSTRACT

A wipe article is provided for cleansing and providing gentle exfoliation. The article is a water-insoluble substrate laden with a fluid cosmetic composition that includes a skin benefit agent delivered in a carrier. The substrate is a woven or non-woven fibrous web with first and second major surfaces, at least one of the major surfaces having formed thereon an array of projections, the array including from at least 2 to about 20 projections per $cm^2$. Each projection is formed of a material different than that of the substrate and is raised from the substrate at a highest point thereof a distance from 100 to 2,000 micron. The projections are formed of at least 20 microbeads per projection.

10 Claims, No Drawings

U.S. PATENT DOCUMENTS

| | | | |
|---|---|---|---|
| 6,375,627 B1 | 4/2002 | Mauze et al. | |
| 6,379,324 B1 | 4/2002 | Gartstein et al. | |
| 6,440,096 B1 | 8/2002 | Lastovich et al. | |
| 6,451,240 B1 | 9/2002 | Sherman et al. | |
| 6,471,903 B2 | 10/2002 | Sherman et al. | |
| 6,476,288 B1 | 11/2002 | VanRijswijck et al. | |
| 6,491,937 B1 | 12/2002 | Slavtcheff et al. | |
| 6,494,830 B1 | 12/2002 | Wessel | |
| 6,506,394 B1 * | 1/2003 | Yahiaoui et al. | 424/402 |
| 6,533,884 B1 | 3/2003 | Malik | |
| 6,565,532 B1 | 5/2003 | Yuzhakov et al. | |
| 6,591,124 B2 | 7/2003 | Sherman et al. | |
| 6,821,281 B2 * | 11/2004 | Sherman et al. | 606/131 |
| 2001/0023324 A1 | 9/2001 | Pronovost et al. | |
| 2001/0029966 A1 | 10/2001 | Wong et al. | |
| 2002/0006355 A1 | 1/2002 | Whitson | |
| 2002/0031486 A1 * | 3/2002 | Lunsmann et al. | 424/70.28 |
| 2002/0045859 A1 | 4/2002 | Gartstein et al. | |
| 2002/0045907 A1 | 4/2002 | Sherman et al. | |
| 2002/0087167 A1 * | 7/2002 | Winitsky | 606/131 |
| 2002/0102392 A1 * | 8/2002 | Fish et al. | 428/198 |
| 2002/0133129 A1 | 9/2002 | Arias et al. | |
| 2002/0177858 A1 | 11/2002 | Sherman et al. | |
| 2002/0192268 A1 * | 12/2002 | Alwattari et al. | 424/443 |
| 2004/0143273 A1 * | 7/2004 | Winitsky | 606/131 |

FOREIGN PATENT DOCUMENTS

| | | |
|---|---|---|
| DE | 196 24 578 A1 | 1/1998 |
| EP | 1 032 366 B1 | 11/1988 |
| EP | 0 312 662 A1 | 4/1989 |
| EP | 0 407 063 A1 | 1/1991 |
| EP | 0 796 128 B1 | 11/1995 |
| EP | 1 086 719 A1 | 3/2001 |
| EP | 1 174 078 A2 | 1/2002 |
| EP | 1 283 019 A1 | 8/2002 |
| EP | 1350456 A1 * | 10/2003 |
| FR | 2535602 A1 | 11/1984 |
| GB | 2221394 | 2/1990 |
| JP | 09-051878 | 2/1997 |
| SU | 1 667 864 | 7/1991 |
| WO | 93/17754 A1 | 9/1993 |
| WO | 94/23777 A1 | 10/1994 |
| WO | 96/00109 A1 | 1/1996 |
| WO | 96/37155 A1 | 11/1996 |
| WO | 96/37256 A1 | 11/1996 |
| WO | 97/03718 A1 | 2/1997 |
| WO | 97/48440 A1 | 12/1997 |
| WO | 97/48441 A1 | 12/1997 |
| WO | 97/48442 A1 | 12/1997 |
| WO | 98/00193 A1 | 1/1998 |
| WO | 99/00155 A1 | 1/1999 |
| WO | 99/29298 A2 | 6/1999 |
| WO | 99/29364 A1 | 6/1999 |
| WO | 99/29365 A1 | 6/1999 |
| WO | 99/64580 A1 | 12/1999 |
| WO | 00/05166 A1 | 2/2000 |
| WO | 00/35530 A1 | 6/2000 |
| WO | 00/74763 A2 | 12/2000 |
| WO | 00/74765 A1 | 12/2000 |
| WO | 00/74766 A1 | 12/2000 |
| WO | 02/07813 A1 | 1/2002 |
| WO | WO 02/072189 A2 | 9/2002 |
| WO | 02/090483 A2 | 11/2002 |
| WO | 03/024290 A1 | 3/2003 |
| WO | 03/024518 A2 | 3/2003 |
| WO | 03/089706 A1 | 10/2003 |

* cited by examiner

EXFOLIATING PERSONAL CARE WIPE ARTICLE CONTAINING AN ARRAY OF PROJECTIONS

BACKGROUND OF THE INVENTION

1. Field of the Invention

The invention concerns a textile impregnated or coated with a personal care cosmetic composition forming an article to exfoliate the face and other parts of the body.

2. The Related Art

Consumers have been presented with many types of wiping articles for use in the personal care of the body. Some are dry articles of a textile coated with a dry cleanser activated to foam upon being wetted at the point of use. Other wipes are textiles soaked in an alcoholic, aqueous or combined mixture of solvents delivering one or more personal care ingredients. These may be foamable or non-foamable. The present invention is concerned with those wipe articles requiring no wetting at the time of use but rather to systems already impregnated with a flowable fluid personal care composition.

U.S. Pat. No. 6,491,937 B1 (Slavtcheff et al.) discloses a foamable product deposited upon a flexible web, the latter including a plurality of moguls spaced apart from one another. The moguls are said to be useful in the manufacture process of the product. One embodiment is a conical or donut shape mogul formed of an elastomeric material which is different than the material forming the web of a substrate.

U.S. Pat. No. 5,971,841 (Tintelnot) reports a flexible, open-pore cleaning article having at least one scouring surface provided in at least one sub-region with continuously formed, raised projecting ridges. Maximum and minimum heights for the ridges are 4 mm and 2 mm, respectively.

U.S. Pat. No. 4,082,878 (Boe et al.) describes an absorbent textile sheet suitable for use as a cleaning cloth. Up to about 70% of the cloth surface is coated with a binding agent present as a three-dimensionally super-elevated printed pattern. A foamed dispersion comprising rubber covers from about 30 to about 70% thereof.

U.S. Pat. No. 3,905,863 (Ayers) discloses a low-density, soft, bulky and absorbent creped paper sheet. A diamond shaped pattern is provided in the surface of the sheet.

U.S. Patent Application 2001/0029966 A1 (Wong et al.) discloses woven or hydro-entangled non-apertured cleaning sheets having non-random recessed and raised regions. This configuration is intended to improve the removal and entrapping of various types of soil.

WO 02/090483 A2 (Allan et al.) reports an impregnated wipe suitable for the cleaning of hard surfaces. The wipe includes on one side a textured abrasive surface formed from nodules and/or striations of abrasive material applied thereon.

EP 1 283 019 A1 (McMeekin et al.) discloses an article containing a substrate with raised elements on at least one surface. The article is useful for providing skin care benefits. The raised elements may be made from hot melt coatings, natural or synthetic rubber, polyolefins, ethylene vinyl acetate or thermoplastic elastomers.

Although the technology of abrasive wipes is extensive as shown by the art discussed above, there still remains a need for a cleansing and make-up remover towelette which achieves gentle exfoliation. The exfoliation should neither be too harsh nor insufficiently effective. Another property sought is that of a wiping article that can efficiently trap the exfoliated human skin cells.

SUMMARY OF THE INVENTION

A wipe article is provided which includes:
(i) a fluid cosmetic composition comprising a skin benefit agent delivered in a cosmetic carrier; and
(ii) a water-insoluble substrate in contact with the cosmetic composition, the substrate being a woven or non-woven fibrous web with first and second major surfaces, at least one of the major surfaces having formed thereon an array of projections, the array comprising from at least 2 to about 20 projections per $cm^2$, each projection formed of a material different than that of the substrate and being raised from the substrate at a highest point thereof a distance from 100 to 2000 micron, and each projection further characterized as comprising a substructure mass of at least 20 microbeads per projection.

DETAILED DESCRIPTION OF THE INVENTION

Now there is provided a wipe article in the form of a towelette capable of cleansing and removing make-up from the skin. The towelette is characterized on at least one surface by an array of projections, preferably regularly patterned with each projection being in the form of massed microbeads. Unlike exfoliating articles of the prior art, the projections formed with microbeads achieve a mild non-harsh exfoliation. Since these projections also through their physical arrangement trap exfoliated cells, they may achieve a clean removal of debris from the skin surfaces.

A first aspect of the present invention is that of a water-insoluble substrate. By "water insoluble" is meant the substrate does not dissolve in or readily break apart upon immersion in water. Another advantage of the substrate is that a skin benefit agent is assisted in penetrating deep down into the skin. The wipe article is also much better than a mere liquid or gel formulation in the accurate application to the skin of benefit agents and avoidance of sensitive areas.

The substrate is a fibrous web with first and second major surfaces. On at least one of these major surfaces there is formed an array of projections. The array includes from at least 2 to about 20 projections per $cm^2$, preferably from about 5 to about 12 projections per $cm^2$. These projections may have any geometry but preferably they have a regular shape. For instance, the shape may be polygonal such as triangular, square, rectangular, pentagonal, hexagonal or substantially rounded. Most preferred for the present invention are substantially rounded projections in the form of dots.

The projections are formed of a material different from that of the substrate. Materials particularly preferred for the projections are synthetic polymers such as polyacrylate, polyurethane, polystyrene, polyolefin and mixtures thereof. Illustrative are homo and copolymers of monomers selected from the group consisting of styrene, butadiene, acrylonitrile, vinyl acetate, vinyl chloride, vinylidene chloride, vinyl pyridine, acrylamide, $C_2$-$C_8$ unsaturated mono- or di-carboxylic acid or ester thereof (e.g. maleic anhydride, acrylic acid, methacrylic acid, ethyl acrylate, ethyl methacrylate), isoprene, divinyl benzene and combinations thereof. The elastomers often are deposited onto the web as an aqueous latex with a drying procedure depositing the projections. Substrates with projections are commercially available from Freudenberg Industries.

Projections according to the present invention each are a mass of microbeads. The number of microbeads per projection can be from at least about 20, preferably at least about 50 and optimally at least 100 per projection. There need be no limitation on the maximum number of microbeads per projection but often the number may range up to about 1,000. At least 50% of the microbeads may have a diameter that ranges from about 1 to about 30 micron, preferably from about 3 to about 20 micron.

Projections of the present invention in one embodiment are prepared by applying a latex of a butadiene-acrylonitrile-methacrylic acid elastomer. The latex in combination with a dispersing surfactant and a foaming agent is formulated with the elastomer. The mixture is applied onto a non-woven textile web through a patterned print screen. The non-woven web then proceeds through a heating process between 40° C. and 70° C. This results in water being removed and the elastomeric mixture expanding.

In a further embodiment, the structures are dots defined as substantially rounded areas of approximately 0.5-1.5 mm diameter. These may be provided with a colorant to have a visual distinction from a differently colored (e.g. white) background textile web. The preferred embodiment utilizes a methacrylate elastomer as the projection material. Preferably the substrates of the present invention are non-apertured meaning that there are no well-defined channels in the substrate of the invention. Advantageously only one side of the textile web is provided with projections.

Compositions of the present invention advantageously will be non-foaming. More particularly, the cosmetic compositions may but not necessarily will have an Average Lather Volume of less than 30 ml. This test is defined in U.S. Pat. No. 6,280,757 B1 (McAtee et al.) herein incorporated by reference. A small amount of emulsifier will however be necessary to achieve emulsification of any water-insoluble components with an aqueous phase under an embodiment where the composition is an emulsion. Thus, cosmetic compositions of the present invention in a preferred embodiment may have from 0% up to 3%, preferably up to only about 1%, and more preferably up to only 0.5% by weight of an emulsifier based on the weight of the cosmetic composition.

A wide variety of materials can be used as the substrate. The following nonlimiting characteristics are desirable: (I) sufficient wet strength for use, (ii) sufficient abrasivity, (iii) sufficient loft and porosity, (iv) sufficient thickness, (v) appropriate size, and (vi) non-reactive with components of the impregnating composition.

Nonlimiting examples of suitable substrates which meet the above criteria include nonwoven substrates, woven substrates, hydroentangled substrates, air entangled substrates and the like. Preferred embodiments employ nonwoven substrates since they are economical and readily available in a variety of materials. By nonwoven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the nonwoven substrate can be composed of a combination of layers of random and carded fibers.

Nonwoven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orlon®; cellulose ester fibers such as cellulose acetate, Arnel®, and Acele°; polyamides such as Nylons (e.g., Nylon 6, Nylon 66, Nylon 610 and the like); polyesters such as Fortrel®, Kodel®, and the polyethylene terephthalate fibers, Dacron®; polyolefins such as polypropylene, polyethylene; polyvinyl acetate fibers and mixtures thereof.

Nonwoven substrates made from natural materials consist of webs or sheets most commonly formed on a fine wire screen from a liquid suspension of the fibers.

Substrates made from natural materials useful in the present invention can be obtained from a wide variety of commercial sources. Nonlimiting examples of suitable commercially available paper layers useful herein include Airtex®, an embossed airlaid cellulosic layer having a base weight of about 71 gsy, available from James River Corporation, Green Bay, Wis.; and Walkisoft®, an embossed airlaid cellulosic having a base weight of about 75 gsy, available from Walkisoft U.S.A., Mount Holly, N.C.

Nonwoven substrates made from synthetic materials useful in the present invention can also be obtained from a wide variety of commercial sources. Nonlimiting examples of suitable nonwoven layer materials useful herein include HEF 40-047, an apertured hydroentangled material containing about 50% rayon and 50% polyester, and having a basis weight of about 43 grams per square yard (gsy), available from Veratec, Inc., Walpole, Mass.; HEF 140-102, an apertured hydroentangled material containing about 50% rayon and 50% polyester, and having a basis weight of about 56 gsy, available from Veratec, Inc., Walpole, Mass.; Novenet® 149-191, a thermo-bonded grid patterned material containing about 69% rayon, about 25% polypropylene, and about 6% cotton, and having a basis weight of about 100 gsy, available from Veratec, Inc., Walpole, Mass.; HEF Nubtex® 149-801, a nubbed, apertured hydroentangled material, containing about 100% polyester, and having a basis weight of about 70 gsy, available from Veratec, Inc. Walpole, Mass.; Keybak® 951 V, a dry formed apertured material, containing about 75% rayon, about 25% acrylic fibers, and having a basis weight of about 43 gsy, available from Chicopee Corporation, New Brunswick, N.J.; Keybak®1368, an apertured material, containing about 75% rayon, about 5% polyester, and having a basis weight of about 39 gsy, available from Chicopee Corporation, New Brunswick, N.J.; Duralace® 1236, an apertured, hydroentangled material, containing about 100% rayon, and having a basis weight from about 40 gsy to about 115 gsy, available from Chicopee Corporation, New Brunswick, N.J.; Duralace® 5904, an apertured, hydroentangled material, containing about 100% polyester, and having a basis weight from about 40 gsy to about 115 gsy, available from Chicopee Corporation, New Brunswick, N.J.; Sontaro® 8868, a hydroentangled material, containing about 50% cellulose and about 50% polyester, and having a basis weight of about 60 gsy, available from Dupont Chemical Corp.

Most preferred as a towelette for purposes of this invention are non-woven substrates, especially blends of hydrophilic and hydrophobic fibers such as rayon/polyester and ratios of 10:90 to 90:10, preferably ratios of 20:80 to 80:20, optimally 40:60 to 60:40 by weight. A most useful towelette is a 70:30 rayon/polyester non-woven wipe article.

Substrates of the present invention can comprise two or more layers, each having a different texture and abrasiveness. The differing textures can result from the use of different combinations of materials. In addition, separate layers of the substrate can be manufactured to have different colors, thereby helping the user to further distinguish the surfaces.

The substrate can be made into a wide variety of shapes and forms. Generally the substrate is in single use towelette form. Advantageously, the towelettes are folded in a Z-shaped formation. They may be interleaved with one another but preferably are not interleaved. The Z fold consists of a center panel flanked by upper and lower wing panels. The upper and lower wing panels are substantially of equal width and substantially half of a width of the center panel. Each towelette is folded medially in a direction orthogonal to that of the Z-shaped formation. Advantageously the size of the towelette may range in length from 10 to 40 cm, preferably from 15 to 30 cm, optimally from 18 to 24 cm. The width of the towelette may range from 8 to 30 cm, preferably from 10 to 25 cm, optimally from 15 to 20 cm.

Anywhere from 5 to 100, preferably from 10 to 50 single towelettes may be stored within a dispensing pouch, preferably a moisture impermeable pouch. During storage and between dispensing, the pouch is resealable, usually via an adhesive strip covering a dispensing opening. Single towelette containing pouches may also be employed.

The amount of cosmetic composition relative to the substrate may range from about 20:1 to 1:20, preferably from 10:1 to about 1:10 and optimally from about 2:1 to about 1:2 by weight.

Cosmetic compositions of the present invention are generally in fluid form. By the term fluid is meant any flowing liquid. Non-limiting viscosity ranges for the composition may range from about 1 to about 500,000, preferably from 5 to 1,000, optimally from 10 to 200 cps, as measured on a Brookfield LVT viscometer (Spindle 4 at 30 rpm and 25° C.).

A skin benefit agent will be present in the cosmetic compositions. Illustrative skin benefit agents include humectants, vitamins, herbal extracts, antimicrobials, emollients and mixtures thereof. Amounts of the skin benefit agent may range from about 0.000001 to about 90%, preferably from about 0.001 to about 95%, optimally from about 0.1 to about 50% by weight depending upon the specific agent.

A variety of cosmetically acceptable carriers may be employed although the carrier normally will be water. Amounts of the carrier may range from about 0.5 to about 99.5%, preferably from about 30 to about 98%, more preferably from about 70 to about 95%, optimally from about 85 to 95% by weight of the composition.

Humectants may be utilized as one of the skin benefit agents according to the present invention. Humectants are normally polyols. Representative polyols include glycerin, diglycerin, polyalkylene glycols and more preferably alkylene polyols and their derivatives including propylene glycol, dipropylene glycol, polypropylene glycol, polyethylene glycol and derivatives thereof, sorbitol, hydroxypropyl sorbitol, hexylene glycol, 1,2-butylene glycol, 1,2,6-hexanetriol, isoprene glycol, ethoxylated glycerol, propoxylated glycerol, 2-methyl-1,3-propanediol and mixtures thereof. Amounts of the polyol may range from about 0.1 to about 95%, preferably from about 0.5 to about 100%, more preferably from about 1 to about 5%, optimally from about 1.5 to about 3% by weight of the composition.

Anti-microbials are another type of skin benefit agent which may be incorporated into the cosmetic compositions of the present invention. Illustrative anti-microbials include triclosan and quaternary ammonium compounds (e.g. cetrimonium chloride). Other types of anti-microbials which can be utilized are alkyl esters of para-hydroxybenzoic acid, hydantoin derivatives, propionate salts and mixtures thereof. Particularly preferred anti-microbials are phenoxyethanol, methyl paraben, propyl paraben, imidazolidinyl urea, sodium dehydroacetate and benzyl alcohol. Anti-microbials are preferably employed in amounts ranging from 0.01% to 2% by weight of the composition.

Compositions of the present invention may further include as a skin benefit agent herbal extracts. Illustrative extracts include Roman Chamomile, Green Tea, Scullcap, Nettle Root, *Swertia Japonica*, Fennel and *Aloe Vera* extracts. Amount of each of the extracts may range from about 0.00001 to about 10%, preferably from about 0.01 to about 0.5%, optimally from about 0.05 to about 0.2% by weight of a composition.

Vitamins and anti-irritant agents may also be utilized as skin benefit agents. Among these may be vitamins such as Vitamin E Acetate, Vitamin C, Vitamin A Palmitate, Panthenol and any of the Vitamin B complexes. Illustrative anti-irritant agents may include those of steviosides, alpha-bisabolol and glycyhrizzinate salts, each vitamin or anti-irritant agent being present in amounts ranging from about 0.0001 to about 1%, preferably from about 0.01 to about 0.3% by weight of the composition.

Emollients may serve as skin benefit agents in the cosmetic compositions of the present invention. General classes of emollients include vegetable or synthetic esters (e.g. lanolin esters and triglycerides such as sunflowerseed oil, tribehenin or polycottonseedate), hydrocarbons (e.g. petrolatum, mineral oil or isoparaffins) and silicones. The silicones may be volatile or non-volatile. Typical volatile silicones are the cyclomethicones commercially available as Dow Corning 244, 245, 344 and 345. Linear volatile dimethicones are also suitable. Non-volatile silicones include polydimethyl siloxanes of a viscosity greater than 2 centistoke and silicone copolyols also known as dimethicone copolyol for which Dow Corning 193 is a commercial source. Amounts of the emollients may range from about 0.01 to about 20%, preferably from about 0.5 to about 3% by weight of the impregnating composition.

Emulsifiers may also be incorporated into compositions of this invention. These emulsifiers may be anionic, nonionic, cationic, amphoteric and combinations thereof. Useful nonionic type emulsifiers include the $C_{10}$-$C_{20}$ fatty alcohol or acid hydrophobes condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic emulsifiers. Particularly preferred as the emulsifier is a hydrogenated castor wax alkoxylated with 40 moles ethylene oxide, available commercially as Cremophore RH40®.

Mild emulsifiers of the anionic and amphoteric type may also be employed. Particularly preferred anionic examples include lauroamphoacetate salts and sarcosinate salts. Preferred amphoterics include cocamidopropylbetaine and dimethylbetaine.

Advantageously it may be desirable to avoid or minimize the presence of any emulsifiers or surfactants because these interact with the skin to accentuate irritation. Emulsifiers and surfactants tend to break the lipid barrier of the skin.

Amounts of the emulsifiers may range from about 0.05 to about 20%, preferably from about 0.1 to about 5%, optimally from about 0.5 to about 2% by weight.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

The following examples will more fully illustrate the embodiments of this invention. All parts, percentages and proportions referred to herein and in the appended claims are by weight unless otherwise illustrated.

EXAMPLES 1-10

An embodiment of the present invention utilizes a rayon/polyester textile "printed" with a dot pattern each dot being approximately 1 mm in diameter. Dots are formed of a puffed polymethacrylate elastomer with approximately 10 dots per $cm^2$ and approximately equally distant from one another. The substrate with dots is available from Freudenberg Industries Inc.

Towelettes sized 15.2 cm by 20.3 cm formed of the above described textile substrate are impregnated each with one of the cosmetic compositions recorded in Table I below. The weight of substrate to cosmetic composition is approximately 1:1 by weight. The resultant towelettes are folded in a Z pattern and packaged within a sealed plastic foil.

touch. Surfaces of varying textures are stroked across a panelists' forearm skin at specified, controlled velocities and forces. After each, the panelist rates the tactile experience along an affective dimension (i.e. from 100% pleasant-to-touch to 100% unpleasant-to-touch). The rating will reflect the impact on the panelist of the different textured surfaces, the velocity of movement, the force of application, the application of the treatment, and the interactions of surface, velocity, force and treatment.

The RTS equipment includes four probes to which textured surfaces are applied. There are two indenting forces specified for each surface stroked across the skin. The surfaces may be stroked across the skin at up to four velocities, stroked in up to two directions (counter clockwise or clockwise). There can be four probes with surfaces of varying texture, two forces, and four vehicles, and two directions creating a maximum of sixty-four Classes. A Block consists of one complete set of all classes. The program allows for the blocks to be repeated as many times as specified.

The Friction Test was also performed on the textile substrates. The protocol required use of an Instron Model 4501 Universal Testing Instrument. The Instron is computer-controlled for test instrument control, data collection and analysis. Tests were run at a controlled humidity and temperature of 50% and 21° C.

The Instron was configured with appropriate fixtures that allowed for the friction between two surfaces to be measured. A metal sled with dimension of 3.1×1.25 inch was attached to the load frame of the machine, while a flat metal plate was fixed on the cross head of the machine. The test textile substrate was placed in the machine direction on the metal plate.

TABLE I

| COMPONENT | EXAMPLE (WEIGHT %) | | | | | | | | | |
|---|---|---|---|---|---|---|---|---|---|---|
| | 1 | 2 | 3 | 4 | 5 | 6 | 7 | 8 | 9 | 10 |
| Phase A | | | | | | | | | | |
| Sodium Lauroamphoacetate | 2.08 | 2.08 | 1.08 | 1.08 | 0.50 | 0.05 | 3.28 | 3.28 | 1.00 | 1.00 |
| Glycerin | 1.00 | 2.00 | 2.00 | 5.00 | 5.00 | 5.00 | 3.00 | 3.00 | 3.00 | 6.00 |
| Polysorbate 20 | 0.50 | 0.50 | 0.50 | 0.50 | 0.50 | 0.50 | 0.50 | 0.50 | 0.50 | 0.50 |
| Cucumber Extract | 0.30 | 0.30 | 0.30 | 0.30 | 0.30 | 0.30 | 0.30 | 0.30 | 0.30 | 0.30 |
| Green Tea Extract | 0.10 | 0.10 | 0.10 | 0.10 | 0.10 | 0.10 | 0.10 | 0.10 | 0.10 | 0.10 |
| Aloe Vera Extract | 0.10 | 0.10 | 0.10 | 0.10 | 0.10 | 0.10 | 0.10 | 0.10 | 0.10 | 0.10 |
| Glydant Plus ® | 0.20 | 0.20 | 0.20 | 0.20 | 0.20 | 0.20 | 0.20 | 0.20 | 0.20 | 0.20 |
| DL-Panthenol | 0.01 | 0.01 | 0.01 | 0.01 | 0.01 | 0.01 | 0.01 | 0.01 | 0.01 | 0.01 |
| Water | To 100 | To 100 | To 100 | To 100 | To 100 | To 100 | To 100 | To 100 | To 100 | To 100 |
| Phase B | | | | | | | | | | |
| Hexylene Glycol | 2.00 | 2.00 | 2.00 | 2.00 | 2.00 | 2.00 | 2.00 | 2.00 | 2.00 | 2.00 |
| PEG-40 Hydrogenated Castor Oil | 0.50 | 0.80 | 0.80 | 0.80 | 0.80 | 0.80 | 1.00 | 1.00 | 0.50 | 0.50 |
| Benzyl Alcohol | 0.40 | 0.40 | 0.40 | 0.40 | 0.40 | 0.40 | 0.40 | 0.40 | 0.40 | 0.40 |
| Fragrance | 0.19 | 0.19 | 0.19 | 0.19 | 0.19 | 0.19 | 0.19 | 0.19 | 0.19 | 0.19 |
| Bisabolol | 0.03 | 0.03 | 0.03 | 0.03 | 0.03 | 0.03 | 0.03 | 0.03 | 0.03 | 0.03 |
| Vitamin E Acetate | 0.001 | 0.001 | 0.001 | 0.001 | 0.001 | 0.001 | 0.001 | 0.001 | 0.001 | 0.001 |

EXAMPLE 11

A set of textiles patterned similar to the substrate Example 1 were evaluated for exfoliation properties. The side of the substrate formed with projections was subjected to a Rotary Tactile Stimulator (RTS) evaluation. The RTS examines attributes of the abrasive surface in terms of non-painful A 200 gram weight was placed on top of the sled. The sled was then placed on the textile substrate and pulled across it at a speed of 10 cm/min.

Sliding friction is the amount of work that is needed to pull the sled over the textile. This was calculated by integrating the area under the Force/Distance curve. The value is recorded as g/cm.

The Table below records RTS parameters of Pleasantness and Texture. In addition, the results of a Friction Test are recorded in the Table along with measured height of the substrate projections.

| Substrate | Friction (g-cm) | Height (micron) | RTS Pleasantness (0-100) | RTS Texture (0-100) |
|---|---|---|---|---|
| Flat Surface | 9.8 | n/a | 5.5 | 5 |
| Sample A | 20.1 | 262 | 50 | 80 |
| Sample B | 8 | 276 | 40 | 40 |
| Sample C | 15.8 | 497 | 90 | 92 |

Samples A and C were identical dot patterns each spaced approximately 3 mm from a nearest dot projection and being approximately 1 mm in diameter. Further Samples A and C had dots which were formed of a mass of at least 20 microbeads per dot. Sample B was physically similar in all but one respect to the Samples A and C. The one difference was the absence of microbeads. Dots of this Sample were an agglomerated mass without microbead formation. The flat surface was not printed with any dots.

It is evident from the results in the Table that panelist attributes of Pleasantness and Texture for Samples A and C were superior to that of Sample B. The presence of microbeads appears to have been the determining factor in the enhanced exfoliation experience.

What is claimed is:

1. A wipe article comprising:
   (i) a fluid cosmetic composition comprising a skin benefit agent delivered in a cosmetic carrier; and
   (ii) a water-insoluble substrate in contact with the cosmetic composition, the substrate being a woven or non-woven fibrous web with first and second major surfaces, at least one of the major surfaces having formed thereon an array of projections, the array comprising from at least 2 to about 20 projections per $cm^2$, each projection formed of a material different than that of the substrate and being raised from the substrate at a highest point thereof a distance from 100 to 2000 micron, and each projection further characterized as comprising a substructure mass of at least 20 microbeads per projection.

2. The article according to claim 1 wherein the substrate is a hydroentangled nonwoven sheet.

3. The article according to claim 1 wherein the substrate is a nonwoven blend of hydrophilic and hydrophobic fibers present in a weight ratio of 10:90 to 90:10.

4. The article according to claim 1 wherein the projections comprise a polymeric material selected from the group consisting of polyacrylate, polyurethane, polystyrene, polyolefin and mixtures thereof.

5. The article according to claim 1 wherein at least 50% of the microbeads range in diameter from about 1 to about 30 micron.

6. The article according to claim 1 wherein the composition and substrate are present in a weight ratio of 20:1 to 1:20.

7. The article according to claim 1 wherein the microbeads range in amount from about 50 to about 1,000 per projection.

8. The article according to claim 1 wherein the carrier is water present in an amount from about 30 to about 98% by weight of a composition.

9. The article according to claim 1 wherein the skin benefit agent is a herbal extract present in amount from 0.00001 to about 1% by weight of the composition.

10. The article according to claim 1 wherein each projection is in a form of a dot.

* * * * *